United States Patent
During

(10) Patent No.: US 10,925,879 B2
(45) Date of Patent: *Feb. 23, 2021

(54) METHODS OF TREATING DEVELOPMENTAL DISORDERS AND/OR SEIZURE DISORDERS WITH ETIFOXINE

(71) Applicant: Ovid Therapeutics Inc., New York, NY (US)

(72) Inventor: Matthew During, Weston, CT (US)

(73) Assignee: Ovid Therapeutics Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/539,081

(22) Filed: Aug. 13, 2019

(65) Prior Publication Data

US 2020/0000813 A1   Jan. 2, 2020

Related U.S. Application Data

(63) Continuation of application No. 15/961,002, filed on Apr. 24, 2018, now Pat. No. 10,420,773.

(60) Provisional application No. 62/563,155, filed on Sep. 26, 2017.

(51) Int. Cl.
| | | |
|---|---|---|
| *A61K 31/536* | (2006.01) | |
| *A61P 25/00* | (2006.01) | |
| *A61P 25/22* | (2006.01) | |
| *A61P 25/28* | (2006.01) | |

(52) U.S. Cl.
CPC .......... *A61K 31/536* (2013.01); *A61P 25/00* (2018.01); *A61P 25/22* (2018.01); *A61P 25/28* (2018.01)

(58) Field of Classification Search
CPC .............................. A61K 31/536; A61P 25/00
See application file for complete search history.

(56) References Cited

U.S. PATENT DOCUMENTS

| 3,725,404 A | 4/1973 | Kuch et al. |
|---|---|---|
| 8,110,569 B2 | 2/2012 | Putman et al. |
| 10,420,773 B2 | 9/2019 | During |
| 2008/0038331 A1 | 2/2008 | Putman |
| 2008/0039453 A1 | 2/2008 | Putman et al. |
| 2016/0244831 A9 | 8/2016 | Hakonarson |

FOREIGN PATENT DOCUMENTS

| WO | 2016154039 A1 | 9/2016 |
|---|---|---|
| WO | 2017070680 A1 | 4/2017 |

OTHER PUBLICATIONS

International Search Report and Written Opinion of the International Searching Authority, dated Dec. 20, 2018, corresponding to counterpart International Application No. PCT/US2018/052542; 7 total pages.

Tvrdeic et al., "Neurosteroids, GABAA receptors and neurosteroid based drugs: are we witnessing the dawn of the new psychiatric drugs," Endocrine Oncology and Metabolism, Mar. 2016; pp. 60-71.

Liu et al., "New differentially expressed genes and differential DNA methylation underlying refractory epilepsy," Oncotarget, vol. 7, No. 52, 2016; pp. 87402-87416.

*Primary Examiner* — Theodore R. Howell

(74) *Attorney, Agent, or Firm* — Carter, DeLuca & Farrell LLP

(57) ABSTRACT

Methods of treating developmental disorders and/or seizure disorders with etifoxine, a deuterated analog of etifoxine, or a pharmaceutically acceptable salt, solvate, or prodrug thereof are provided. The methods provide therapeutic compositions that may be used to improve one or more symptoms of the developmental disorder and/or seizure disorder.

32 Claims, No Drawings

METHODS OF TREATING DEVELOPMENTAL DISORDERS AND/OR SEIZURE DISORDERS WITH ETIFOXINE

CROSS-REFERENCE TO RELATED APPLICATIONS

This application is a continuation application of U.S. patent application Ser. No. 15/961,002, filed Apr. 24, 2018, issued as U.S. Pat. No. 10,420,773 on Sep. 24, 2019, which claims benefit of and priority to U.S. Provisional Application No. 62/563,155, filed Sep. 26, 2017, which are incorporated herein by reference in their entirety.

TECHNICAL FIELD

Methods of treating developmental disorders and/or seizure disorders with etifoxine are provided.

BACKGROUND

Treatments for developmental disorders such as Autistic Spectrum Disorder, Dravet syndrome, Rett syndrome, Angelman syndrome, Fragile X syndrome, and Fragile X-associated tremor/ataxia syndrome are limited. Angelman syndrome is a neurodevelopmental disorder caused by loss of function of the UBE3A gene encoding a ubiquitin E3 ligase. Motor dysfunction is a characteristic feature of Angelman syndrome, but neither the mechanisms of action nor effective therapeutic strategies have yet been elucidated.

Fragile X syndrome may be the most common genetic cause of intellectual disability and the most common single-gene cause of autism. It is caused by mutations on the fragile X mental retardation gene (FMR1) and lack of fragile X mental retardation protein, which in turn, leads to decreased inhibition of translation of many synaptic proteins. The main efforts have focused on metabotropic glutamate receptor (mGluR) targeted treatments; however, investigation on the gamma-aminobutyric acid (GABA) system and its potential as a targeted treatment is less emphasized. The fragile X mouse models (Fmr1-knock out) show decreased GABA subunit receptors, decreased synthesis of GABA, increased catabolism of GABA, and overall decreased GABAergic input in many regions of the brain. These symptoms are also observed in individuals with autism and other neurodevelopmental disorders, therefore the targeted treatments for Fragile X syndrome are leading the way in the treatment of other neurodevelopmental syndromes and autism. Potential GABAergic treatments, such as riluzole, gaboxadol, tiagabine, and vigabatrin have been discussed. However, further studies are needed to determine the safety and efficacy of GABAergic treatments for Fragile X syndrome.

Fragile X-associated tremor/ataxia syndrome (FXTAS) is a late-onset disorder, usually occurring after age 50. Mutations in the FMR1 gene increase the risk of developing FXTAS. The mutation relates to a DNA segment known as a CGG triplet repeat which is expanded within the FMR1 gene. Normally, this DNA segment is repeated from 5 to about 40 times. In people with FXTAS the CGG segment may be repeated 55 to 200 times. This mutation is known as an FMR1 gene premutation. An expansion of more than 200 repeats, a full mutation, causes Fragile X syndrome discussed above. FXTAS is typically characterized by problems with movement and thinking ability (cognition). FXTAS signs and symptoms usually worsen with age. Affected individuals have areas of damage in the cerebellum, the area of the brain that controls movement. Characteristic features of FXTAS are intention tremor, which is trembling or shaking of a limb when trying to perform a voluntary movement such as reaching for an object, and problems with coordination and balance (ataxia). Many affected individuals develop other movement problems, such as parkinsonism, which includes tremors when not moving (resting tremor), rigidity, and unusually slow movement (bradykinesia). In addition, affected individuals may have reduced sensation, numbness or tingling, pain, or muscle weakness in the lower limbs, and inability to control the bladder or bowel. Other symptoms may include chronic pain syndromes, such as fibromyalgia and chronic migraine, hypothyroidism, hypertension, insomnia, sleep apnea, vertigo, olfactory dysfunction, and hearing loss. People with FXTAS commonly have cognitive disabilities such as short-term memory loss and loss of executive function, which is the ability to plan and implement actions and develop problem-solving strategies. Loss of this function impairs skills such as impulse control, self-monitoring, focusing attention appropriately, and cognitive flexibility. Many people with FXTAS experience psychiatric symptoms such as anxiety, depression, moodiness, or irritability.

There is currently no targeted therapeutic intervention that can arrest or reverse the pathogenesis of FXTAS. However a number of treatment approaches of potential symptomatic benefit have been suggested. Primidone, beta-blockers such as propanolol, topiramate, carbidopa/levodopa, and benzodiazepines have been suggested to control tremors associated with FXTAS; botulinum toxin for involuntary muscle activities, such as dystonia and spasticity; carbidopa/levodopa, amantadine and buspirone for ataxia; cholinesterase inhibitors such as donepezil, and memantine (an NMDA antagonist) for cognitive deficits and dementia; and antidepressants and antipsychotics for psychiatric symptoms. See, e.g., Hagerman, et al., Clin Intery Aging. 2008 June; 3(2): 251-262.

Rett syndrome is a neurodevelopmental disorder that typically affects girls. It is characterized by normal early growth and development followed by a slowing of development, loss of purposeful use of the hands, distinctive hand movements, slowed brain and head growth, problems with walking, seizures, and intellectual disability. Nearly all cases of Rett syndrome are caused by a mutation in the methyl CpG binding protein 2, or MECP2 gene. The MECP2 gene contains instructions for the synthesis of methyl cytosine binding protein 2 (MeCP2), which is utilized in brain development and acts as one of the many biochemical switches that can either increase or decrease gene expression. The main diagnostic criteria or symptoms include partial or complete loss of acquired purposeful hand skills, partial or complete loss of acquired spoken language, repetitive hand movements (such has hand wringing or squeezing, clapping or rubbing), and gait abnormalities, including toe-walking or an unsteady, wide-based, stiff-legged walk. Supportive criteria are not required for a diagnosis of Rett syndrome but may occur in some individuals. In addition, these symptoms, which vary in severity from child to child, may not be observed in very young children but may develop with age. A child with supportive criteria but none of the essential criteria does not have Rett syndrome. Supportive criteria include scoliosis, teeth-grinding, small cold hands and feet in relation to height, abnormal sleep patterns, abnormal muscle tone, heart abnormalities, inappropriate laughing or screaming, intense eye communication, and diminished response to pain.

There is no cure for Rett syndrome. Treatment for the disorder is symptomatic, focusing on the management of symptoms, and supportive, requiring a multidisciplinary approach. Medication may be needed for breathing irregularities and motor difficulties, and anticonvulsant drugs may be used to control seizures.

Dravet syndrome, also known as Severe Myoclonic Epilepsy of Infancy (SMEI) is a severe form of intractable epilepsy that begins in infancy with febrile seizures. Later, patients also manifest other seizure types, including absence, myoclonic, and partial seizures. The EEG is often normal at first, but later characteristically shows generalized spike-wave activity. Psychomotor development stagnates around the second year of life, and affected individuals show subsequent mental decline and other neurologic manifestations. Dravet syndrome is associated with ataxia, slowed psychomotor development, and mental decline, and is often refractory to medication. Dravet syndrome has been associated with mutation of the SCN1A gene on chromosome 2q24.

Accordingly, there remains a need for effective treatments of patients with developmental disorders, such as Autistic Spectrum Disorder, pervasive developmental disorder, Autism, Angelman syndrome, Fragile X syndrome, Fragile X-associated tremor/ataxia syndrome (FXTAS), Rett syndrome, Asperger's syndrome, Childhood Disintegrative Disorder, Attention-deficit/hyperactivity disorder (ADHD), Prader-Willi Syndrome, Landau-Kleffner Syndrome, Rasmussen's syndrome, Dravet syndrome, Tardive Dyskinesia, Williams Syndrome and/or seizure disorders per se, and/or seizure disorders associated with any of the foregoing developmental disorders.

Seizure disorders typically involve abnormal nerve cell activity in the brain, causing seizures which may be manifested by periods of unusual behavior, sensations, diminished consciousness and sometimes loss of consciousness. Seizures can be a symptom of many different disorders that can affect the brain. Epilepsy is a seizure disorder characterized by recurrent seizures. See, e.g., Blume et al., Epilepsia. 2001; 42:1212-1218. Epileptic seizures are usually marked by abnormal electrical discharges in the brain and typically manifested by sudden brief episodes of altered or diminished consciousness, or involuntary movements. Non-epileptic seizures may or may not be accompanied by abnormal electrical activity in the brain and may be caused by psychological issues or stress. Drug or alcohol withdrawal can also cause seizures. Seizure symptoms can vary widely. Some seizures can hardly be noticed, while others are totally disabling. Seizure disorders include epilepsy.

Medications are used to treat seizure disorders and can be referred to as anti-epileptic drugs ("AED"). The treatment of recurrent seizures predominantly centers on the utilization of at least one AED, with possible adjunctive use of a second or even third agent in the case of monotherapeutic failure. See, Tolman and Faulkner, Ther Clin Risk Manag. 2011; 7: 367-375. However, approximately 30%-40% of epileptic patients have inadequate seizure control with just one AED, and require the use of adjunctive agents. Id. A subset of this group will have regular and persistent seizure activity despite reasonable doses of multiple AEDs. These seizures are considered refractory to treatment. Id. Accordingly, there remains a need for improved and/or additional therapies for treating seizure disorders.

SUMMARY

Methods of treating a developmental disorder described herein include administering at least one compound selected from the group consisting of etifoxine, a deuterated analog of etifoxine, or a pharmaceutically acceptable salt thereof, to a patient in need thereof to provide improvement in one or more symptoms of the developmental disorder. In embodiments, methods of treating a developmental disorder described herein include administering at least one etifoxine selected from R-etifoxine, S-etifoxine, and combinations thereof. In embodiments, methods of treating a developmental disorder described herein include administering at least one deuterated analog of etifoxine of formula I below:

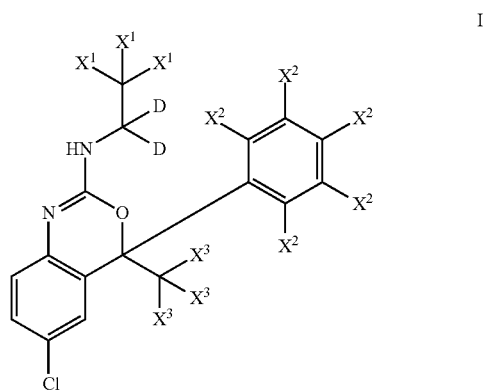

including pharmaceutically acceptable salts, wherein each $X^1$, $X^2$, $X^3$ are independently selected from the group consisting of hydrogen and deuterium. In embodiments, the deuterated analog of etifoxine is selected from deuterated R-etifoxine, deuterated S-etifoxine, and combinations thereof.

In embodiments, methods of treating a developmental disorder described herein include administering at least one compound selected from the group consisting of etifoxine, a deuterated analog of etifoxine, or a pharmaceutically acceptable salt thereof to a patient in need thereof to provide improvement in next day functioning of the patient. In embodiments, methods of treating a developmental disorder described herein include administering at least one etifoxine selected from R-etifoxine, S-etifoxine, and combinations thereof. In embodiments, methods of treating a developmental disorder described herein include administering at least one deuterated analog of etifoxine of formula I below:

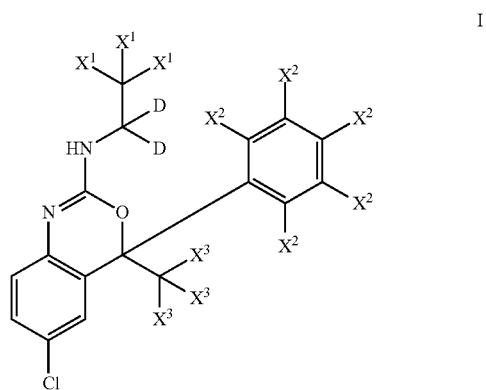

including pharmaceutically acceptable salts, wherein each $X^1$, $X^2$, $X^3$ are independently selected from the group consisting of hydrogen and deuterium. In embodiments, the deuterated analog of etifoxine is selected from deuterated R-etifoxine, deuterated S-etifoxine, and combinations thereof.

In embodiments, the developmental disorder may be an Autistic Spectrum Disorder, pervasive developmental disorder, Autism, Angelman syndrome, Fragile X syndrome, Fragile X-associated tremor/ataxia syndrome (FXTAS), Rett syndrome, Asperger's syndrome, Childhood Disintegrative Disorder, Attention-deficit/hyperactivity disorder (ADHD), Prader-Willi Syndrome, Landau-Kleffner Syndrome, Rasmussen's syndrome, Dravet syndrome, 22q11.2 syndrome, Tardive Dyskinesia, Williams Syndrome and/or seizure disorders per se, and/or seizure disorders associated with any of the foregoing developmental disorders. Examples of seizure disorders include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Doose syndrome, CDKL5 disorder, West syndrome, Lennox-Gastaut syndrome (LGS), Rett syndrome, Ohtahara syndrome, CDKL5 disorder, childhood absence epilepsy, essential tremor, and acute repetitive seizures, benign rolandic epilepsy, status epilepticus, refractory status, epilepticus, super-refractory status epilepticus (SRSE), PCDH19 pediatric epilepsy, increased seizure activity or breakthrough seizures (increased seizure activity: also called serial or cluster seizures). Seizure disorders include sodium channel protein type 1 subunit alpha (Scn1a)-related disorders.

Methods of treating a seizure disorder are also provided and, in embodiments, include administering to a subject in need thereof at least one compound selected from the group consisting of etifoxine, a deuterated analog of etifoxine, or a pharmaceutically acceptable salt thereof.

In embodiments, methods of treating a seizure disorder include administering at least one compound selected from the group consisting of etifoxine, a deuterated analog of etifoxine, or a pharmaceutically acceptable salt thereof to a subject in need thereof to provide improvement in one or more symptoms of the seizure disorder. In embodiments, methods of treating a seizure disorder described herein include administering at least one etifoxine selected from R-etifoxine, S-etifoxine, and combinations thereof. In embodiments, methods of treating a seizure disorder described herein include administering at least one deuterated analog of etifoxine of formula I below:

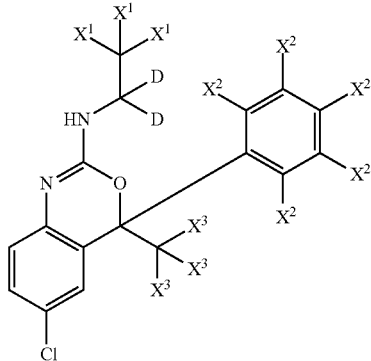

including pharmaceutically acceptable salts, wherein each $X^1$, $X^2$, $X^3$ are independently selected from the group consisting of hydrogen and deuterium. In embodiments, the deuterated analog of etifoxine is selected from deuterated R-etifoxine, deuterated S-etifoxine, and combinations thereof.

In embodiments, methods of treating a seizure disorder include administering at least one compound selected from the group consisting of etifoxine, a deuterated analog of etifoxine, or a pharmaceutically acceptable salt thereof to a subject in need thereof to provide improvement in next day functioning of the subject. In embodiments, methods of treating a seizure disorder described herein include administering at least one etifoxine selected from R-etifoxine, S-etifoxine, and combinations thereof. In embodiments, methods of treating a seizure disorder described herein include administering at least one deuterated analog of etifoxine of formula I below:

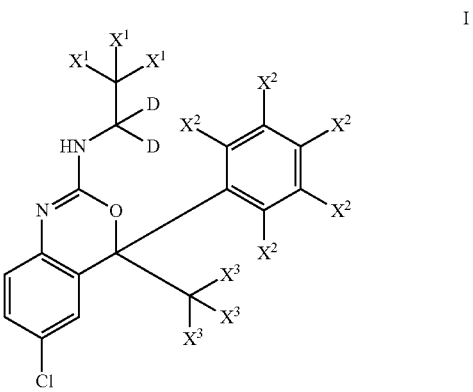

including pharmaceutically acceptable salts thereof, wherein each $X^1$, $X^2$, $X^3$ are independently selected from the group consisting of hydrogen and deuterium. In embodiments, the deuterated analog of etifoxine is selected from deuterated R-etifoxine, deuterated S-etifoxine, and combinations thereof.

In embodiments, the seizure disorders treated in accordance with the present disclosure include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (increased seizure activity; also called serial or cluster seizures).

Methods of treating a developmental encephalopathy are also provided and, in embodiments, include administering to a subject in need thereof at least one compound selected from the group consisting of etifoxine, a deuterated analog of etifoxine, or a pharmaceutically acceptable salt thereof.

In embodiments, at least one of etifoxine, R-etifoxine, S-etifoxine, a deuterated analog of etifoxine, or a pharmaceutically acceptable salt thereof is administered to the subject from one to six times a day. Administration may be by any appropriate route, including oral, buccal, sublingual, rectal, topical, intranasal, vaginal, parenteral, combinations thereof, and the like.

DETAILED DESCRIPTION

Described herein are methods of treating a developmental disorder that include administering at least one compound selected from the group consisting of etifoxine, a deuterated analog of etifoxine, or a pharmaceutically acceptable salt thereof to a patient in need thereof to provide improvement in one or more symptoms of the disorder. In embodiments, methods of treating a developmental disorder described herein include administering at least one compound selected from the group consisting of etifoxine, a deuterated analog of etifoxine, or a pharmaceutically acceptable salt thereof to a patient in need thereof to provide improvement in next day functioning of the patient. Described herein are methods of treating a seizure disorder that include administering at least one compound selected from the group consisting of etifoxine, a deuterated analog of etifoxine, or a pharmaceutically acceptable salt thereof to a patient in need thereof to provide improvement in one or more symptoms of the disorder. In embodiments, methods of treating a seizure disorder described herein include administering at least one compound selected from the group consisting of etifoxine, a deuterated analog of etifoxine, or a pharmaceutically acceptable salt thereof to a patient in need thereof to provide improvement in next day functioning of the patient. In embodiments, methods of treating a developmental disorder and/or a seizure disorder include administering at least one compound selected from the group consisting of etifoxine, a deuterated analog of etifoxine, or a pharmaceutically acceptable salt thereof to a patient in need thereof. In embodiments, methods of treating a developmental disorder and/or a seizure disorder include administering a pharmaceutical composition containing at least one of etifoxine, a deuterated analog of etifoxine, or a pharmaceutically acceptable salt thereof to a patient in need thereof. In embodiments, methods of treating a developmental disorder and/or a seizure disorder include administering a pharmaceutical composition containing at least one of etifoxine, a deuterated analog of etifoxine, or a pharmaceutically acceptable salt thereof to a patient in need thereof to provide improvement in one or more symptoms of the disorder. In embodiments, methods of treating a developmental disorder and/or a seizure disorder described herein include administering a pharmaceutical composition containing at least one of etifoxine, a deuterated analog of etifoxine, or a pharmaceutically acceptable salt thereof to a patient in need thereof to provide improvement in next day functioning of the patient.

In embodiments, the developmental disorder may be an Autistic Spectrum Disorder, pervasive developmental disorder, autism, Angelman syndrome, Fragile X syndrome, Fragile X-associated tremor/ataxia syndrome (FXTAS), Rett syndrome, Asperger's syndrome, Childhood Disintegrative Disorder, Attention-deficit/hyperactivity disorder (ADHD), Prader-Willi Syndrome, Landau-Kleffner Syndrome, Rasmussen's syndrome, Dravet syndrome, Tardive Dyskinesia, 16p11.2 deletion syndrome, 16p11.2 recurrent microdeletion, Albright hereditary osteodystrophy, Alstrom syndrome, Bardet-Biedl syndrome, Borjeson-Forssman-Lehmann syndrome, Cohen syndrome, Down syndrome, Klinefelter syndrome, Turner syndrome, Smith-Magenis syndrome, 21-Hydroxylase-Deficient Congenital Adrenal Hyperplasia, 2q37 Microdeletion syndrome, 3q29 Recurrent Deletion, Achondroplasia, ADNP-Related Intellectual Disability and melanocortin 4 receptor (MC4R) deficiency, Williams Syndrome and/or seizure disorders per se, and/or seizure disorders independent of, or associated with, any of the foregoing developmental disorders.

In embodiments, the developmental disorder is Angelman syndrome.

In embodiments, the developmental disorder is Fragile X syndrome.

In embodiments, the developmental disorder is Rett syndrome.

In embodiments, the development disorder is a developmental encephalopathy. Some non-limiting examples include tuberous sclerosis, early myoclonic encephalopathy, and early-onset epileptic encephalopathy.

In embodiments, the developmental disorder is a developmental encephalopathy associated with a genetic mutation of a one or more of the following genes: ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDCS, DNM1, EEF1A2, EPM2A, FLNA, FOXG1 duplications, GABRA1, GABRB3, GABRG2, GLI3, GNAO1, GOSR2, GRIN1, GRIN2A, GRIN2B, GRIN2D, HCN1, HNRNPU, IER3IP1, IQSEC2, KCNA2, KCNB1, KCNC1, KCNMA1, KCNQ2, KCNQ3, KCNT1, KCTD7, LGI1, MAGI2, MEF2C, NEDDL4, NDP, NHLRC1, NRXN1, PCDH19, PIGA, PIGQ, PLCB1, PNKP, PNPO, PRICKLE1, PRICKLE2, PRRT2, PTEN, *PURA*, QARS, RELN, SCA2, SCARB2, SCN1A, SCN1B, SCN2A, SCN8A, SCN9A, SETBP1, SIAT9, SIK1, SLC12A5, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, TCF4 and WWOX encephalopathy. In embodiments, the developmental disorder is a developmental encephalopathy associated with a genetic mutation of the CDKL5 gene. In embodiments, the developmental disorder is a developmental encephalopathy associated with a genetic mutation of the PCDH19 gene.

In embodiments, the developmental disorder is a neurodevelopmental disorder. Some non-limiting examples of neurodevelopmental disorders include 22Q syndrome, such as 22q11.2 syndrome and/or 22q11.2 duplication syndrome, DiGeorge syndrome (DGS), DiGeorge anomaly, velocardiofacial syndrome (VCFS), conotruncal anomaly face syndrome (CTAF), Opitz G/BBB syndrome, Cayler cardiofacial syndrome, Shprintzen syndrome, Takao syndrome, Sedlackova syndrome, Strong syndrome, congenital thymic aplasia, and thymic hypoplasia.

In embodiments, the developmental disorder is an intellectual developmental disability (IDD), such as Autism Spectrum Disorder (ASD). In embodiments, the patient of the disclosed method has developmental encephalopathy and an IDD or ASD disorder. Common IDD and ASD that are comorbid with developmental encephalopathies include, but are not limited to, fragile X syndrome (FXS), Rett syndrome (RTT), Angelman syndrome, Prader-Willi syndrome, Velocardiofacial syndrome, Smith-Lemli-Opitz syndrome, neuroligin mutations and "interneuronopathies" resulting from aristaless-related homeobox, X-linked (ARX) and Nueropilin 2 (NRP2) gene mutations.

In embodiments, the seizure disorder may include epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, catastrophic epilepsy, increased seizure activity or breakthrough seizures (also called serial or cluster seizures). In embodiments, the seizure disorder is associated with a sodium channel protein type 1 subunit alpha (Scn1a)-related disorder. Scn1a-related disorders include generalized epilepsy with febrile seizures plus, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome (LGS), infantile spasms, and vaccine-related encephalopathy and seizures.

In embodiments, the seizure disorder is status epilepticus (SE). SE is characterized by an epileptic seizure of greater than five minutes or more than one seizure within a five-minute period without the person returning to normal between them. SE can be a dangerous condition that can lead to mortality if treatment is delayed. SE can be convulsive, with a regular pattern of contraction and extension of the arms and legs, or non-convulsive, with a change in a person's level of consciousness of relatively long duration but without large scale bending and extension of the limbs due to seizure activity. Convulsive SE (CSE) may be further classified into (a) tonic—clonic SE, (b) tonic SE, (c) clonic SE and (d) myoclonic SE. Non-convulsive SE (NCSE) is characterized by abnormal mental status, unresponsiveness, ocular motor abnormalities, persistent electrographic seizures, and possible response to anticonvulsants.

In embodiments, the seizure disorder is a CDKL5 disorder.

In embodiments, the seizure disorder is a PCDH19 disorder.

In embodiments, the disorder is a combination of disorders. For example, the methods described herein may be used to treat both a developmental disorder and a seizure disorder.

Symptoms of developmental disorders and/or seizure disorders may include, but are not limited to, episodes involving ataxia, gait impairment, speech impairment, vocalization, impaired cognition, abnormal motor activity, clinical seizure, subclinical seizure, hypotonia, hypertonia, drooling, and mouthing behavior, aura, repetitive movements, and unusual sensations. In embodiments, the methods and compositions described herein may reduce or prevent one or more different symptoms related to the disorder.

Symptoms of a seizure disorder may include, but are not limited to, episodes involving ataxia, gait impairment, speech impairment, vocalization, impaired cognition, abnormal motor activity, clinical seizure, subclinical seizure, hypotonia, hypertonia, drooling, and mouthing behavior, aura, repetitive movements, and unusual sensations. In embodiments, the methods and compositions provided may reduce or prevent one or more different types of seizures. Generally, a seizure can include repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

The methods of treatment described herein include administering at least one compound selected from the group consisting of etifoxine, a deuterated analog of etifoxine, or a pharmaceutically acceptable salt, solvate, hydrate or prodrug thereof to a patient.

Etifoxine is a chiral molecule that has been used as a racemate. Etifoxine is 6-chloro-2-(ethylamino)-4-methyl-4-phenyl-4H-3,1-benzoxazine and can be represented by the following chemical structure:

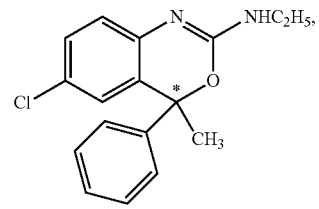

where * indicates the chiral center in the molecule.

Etifoxine hydrochloride is represented as:

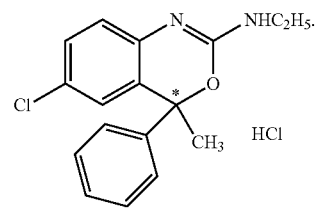

U.S. Pat. No. 3,725,404 describes various methods of preparing and using etifoxine as racemic mixture, the contents of which are hereby incorporated by reference in their entirety.

In embodiments, the compound includes at least one etifoxine directed to the chemical structure represented below:

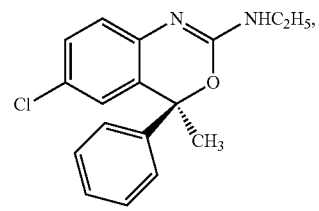

or a pharmaceutically acceptable salt, solvate, hydrate or prodrug thereof.

In embodiments, the compound includes at least one etifoxine directed to the chemical structure represented below:

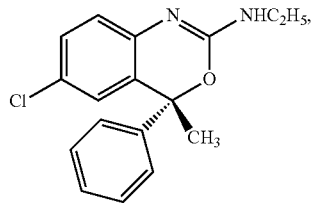

or a pharmaceutically acceptable salt, solvate, hydrate or prodrug thereof.

(+)-Etifoxine and/or R-etifoxine corresponds to the R enantiomer of etifoxine. (−)-Etifoxine and/or S-etifoxine corresponds to the S enantiomer of etifoxine. In embodiments, the compound may be (+)-Etifoxine. In embodiments, the compound may be (−)-Etifoxine. In embodiments, the at least one compound may include a combination of R-efifoxine and S-etifoxine.

In embodiments, the compound is selected from enantiomerically pure R-etifoxine and pharmaceutically acceptable salts, solvates, hydrates and prodrugs thereof. In embodiments, the compound is selected from enantiomerically pure R-etifoxine and pharmaceutically acceptable salts thereof. In embodiments, the compound is R-etifoxine hydrochloride.

In embodiments, the enantiomerically pure R-etifoxine comprises at least about 80% by weight R-etifoxine and at most about 20% by weight S-etifoxine, at least about 90% by weight R-etifoxine and at most about 10% by weight S-etifoxine, at least about 95% by weight R-etifoxine and at most about 5% by weight S-etifoxine, at least about 96.6% by weight R-etifoxine and at most about 3.4% by weight S-etifoxine, at least about 97% by weight R-etifoxine and at most about 3% by weight S-etifoxine, at least about 99% by weight R-etifoxine and at most about 1% by weight S-etifoxine or at least about 99.9% by weight R-etifoxine and at most about 0.1% by weight S-etifoxine. In one embodiment, the pure R-etifoxine comprises at least about 96.6% by weight R-etifoxine and at most about 3.4% by weight S-etifoxine, at least about 97% by weight R-etifoxine and at most about 3% by weight S-etifoxine, at least about 98% by weight R-etifoxine and at most about 2% by weight S-etifoxine or at least about 99% by weight R-etifoxine and at most about 1% by weight S-etifoxine. In embodiments, the weights are based upon total weight of etifoxine.

In embodiments, the compound is selected from enantiomerically pure S-etifoxine and pharmaceutically acceptable salts, solvates, hydrates and prodrugs thereof. In embodiments, the compound is selected from enantiomerically pure S-etifoxine and pharmaceutically acceptable salts thereof. In embodiments, the compound is S-etifoxine hydrochloride.

In embodiments, the enantiomerically pure S-etifoxine comprises at least about 80% by weight S-etifoxine and at most about 20% by weight R-etifoxine, at least about 90% by weight S-etifoxine and at most about 10% by weight R-etifoxine, at least about 95% by weight S-etifoxine and at most about 5% by weight R-etifoxine, at least about 96.6% by weight S-etifoxine and at most about 3.4% by weight R-etifoxine, at least about 97% by weight S-etifoxine and at most about 3% by weight R-etifoxine, at least about 99% by weight S-etifoxine and at most about 1% by weight R-etifoxine or at least about 99.9% by weight S-etifoxine and at most about 0.1% by weight R-etifoxine. In one embodiment, the pure S-etifoxine comprises at least about 96.6% by weight S-etifoxine and at most about 3.4% by weight R-etifoxine, at least about 97% by weight S-etifoxine and at most about 3% by weight R-etifoxine, at least about 98% by weight S-etifoxine and at most about 2% by weight R-etifoxine or at least about 99% by weight S-etifoxine and at most about 1% by weight R-etifoxine. In embodiments, the weights are based upon total weight of etifoxine.

In embodiments, the compound is a deuterated analog of etifoxine. In embodiments, the compound is a deuterated analog of R-etifoxine. In embodiments, the compound is a deuterated analog of S-etifoxine.

In embodiments, the deuterated analog of etifoxine is directed to compounds of Formula IA:

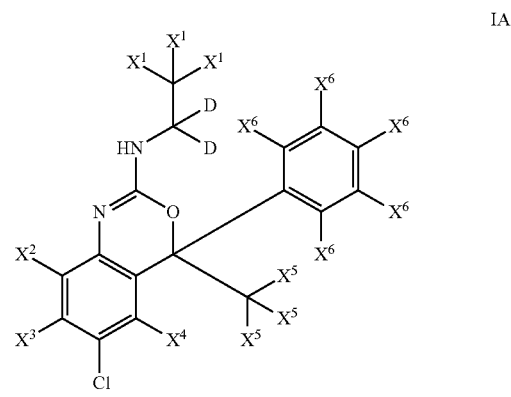

and pharmaceutically acceptable salts, solvates, and prodrugs thereof, wherein: each $X^1$, $X^2$, $X^3$, $X^4$, $X^5$ and $X_6$ are independently selected from hydrogen and deuterium.

In embodiments, in such compounds of Formula IA, each $X^1$ is deuterium.

In embodiments, the compounds of Formula IA have each $X^1$ is hydrogen.

In embodiments, $X^2$, $X^3$, $X^4$, $X^5$ and $X^6$ are hydrogen such that the deuterated analog of etifoxine is a compound having the structure of Formula IIA:

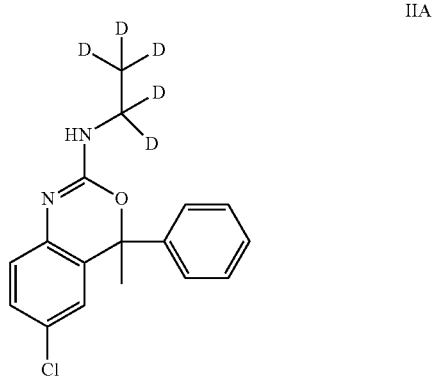 [SMILES: [2H]C([2H])([2H])C([2H])([2H])NC1=Nc2ccc(Cl)cc2C(C)(c2ccccc2)O1]

and pharmaceutically acceptable salts, solvates, and prodrugs thereof.

In one such embodiment, $X^1$, $X^2$, $X^3$, $X^4$, $X^5$ and $X_6$ are hydrogen such that the deuterated analog of etifoxine is a compound having the structure of Formula IIIA:

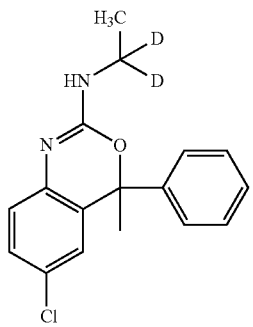

IIIA and pharmaceutically acceptable salts, solvates, and prodrugs thereof.

In embodiments, the compounds of Formula IA have each $X^1$ and each $X^6$ as deuterium. In one such embodiment, $X^2$, $X^3$, $X^4$ and $X^5$ are hydrogen such that the deuterated analog of etifoxine is a compound having the structure of Formula IVA:

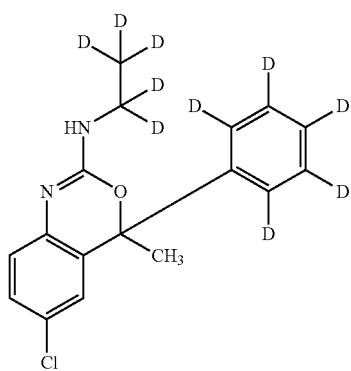

IVA and pharmaceutically acceptable salts, solvates, and prodrugs thereof.

In embodiments, compounds of Formula IA have each $X^1$ and each $X^5$ are deuterium. In one such embodiment, $X^2$, $X^3$, $X^4$ and $X^6$ are hydrogen such that the deuterated analog of etifoxine is a compound having the structure of Formula VA:

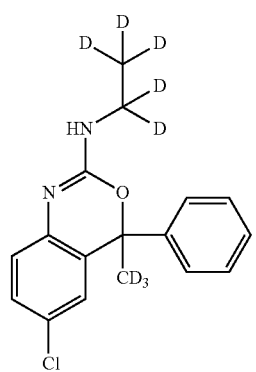

VA and pharmaceutically acceptable salts, solvates, and prodrugs thereof.

In embodiments, compounds of Formula IA have each $X^1$, $X^2$, $X^3$, $X^4$, and $X^6$ are deuterium. In one such embodiment, $X^5$ and $X_6$ are hydrogen such that the deuterated analog of etifoxine is a compound having the structure of Formula VIA:

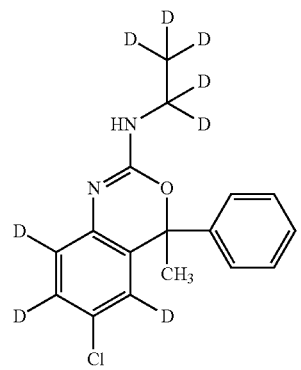

VIA and pharmaceutically acceptable salts, solvates, and prodrugs thereof.

In embodiments, compounds of Formula IA have each $X^1$, $X^5$, and $X^6$ are deuterium. In one such embodiment, $X^2$, $X^3$ and $X^4$ are hydrogen such that the deuterated analog of etifoxine is a compound having the structure of Formula VIIA:

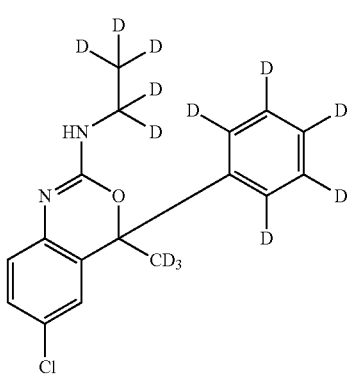

VIIA and pharmaceutically acceptable salts, solvates, and prodrugs thereof.

In embodiments, the compound is directed to compounds of Formula IB:

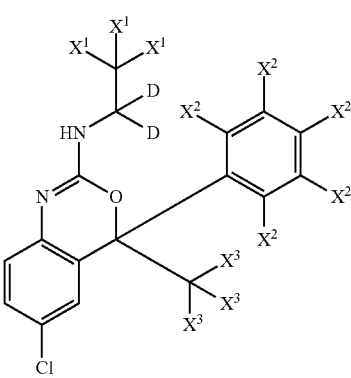

I and pharmaceutically acceptable salts, solvates, and prodrugs thereof, wherein: each of $X^1$, $X^2$ and $X^3$ are independently selected from hydrogen and deuterium. In one embodiment, in such compounds each $X^1$ is deuterium.

In embodiments, each $X^2$ and $X^3$ are hydrogen such that the deuterated analog of etifoxine is a structure of Formula IIB below:

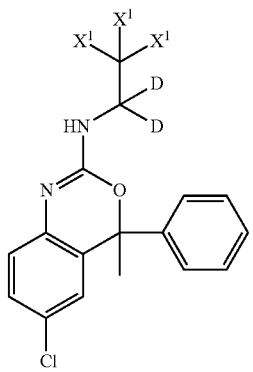

and pharmaceutically acceptable salts, solvates, and prodrugs thereof.

In embodiments the deuterated analog of etifoxine is 6-chloro-N-(ethyl-d5)-4-methyl-4-phenyl-4H-3,1-benzoxazin-2-amine and pharmaceutically acceptable salts, solvates, and prodrugs thereof.

In embodiments the deuterated analog of etifoxine is 6-chloro-N-(ethyl-d5)-4-methyl-4-(phenyl-d5)-4H-3,1-benzoxazin-2-amine and pharmaceutically acceptable salts, solvates, and prodrugs thereof.

In embodiments the deuterated analog of etifoxine is 6-chloro-N-(ethyl-d5)-4-(methyl-d3)-4-(phenyl-d5)-4H-3,1-benzoxazin-2-amine and pharmaceutically acceptable salts, solvates, and prodrugs thereof.

In embodiments the deuterated analog of etifoxine is 6-chloro-V-(ethyl-1,1-d2)-4-methyl-4-phenyl-4H-3,1-benzoxazin-2-amine and pharmaceutically acceptable salts, solvates, and prodrugs thereof.

In embodiments, a compound of Formulae I-II described hereinabove and 6-chloro-N-(ethyl-ds)-4-methyl-4-phenyl-4H-3,1-benzoxazin-2-amine; 6-chloro-N-(ethyl-d5)-4-methyl-4-(phenyl-d5)-4H-3,1-benzoxazin-2-amine; 6-chloro-N-(ethyl-d5)-4-(methyl-d3)-4-(phenyl-d5)-4H-3,1-benzoxazin-2-amine; or 6-chloro-V-(ethyl-1,1-d2)-4-methyl-4-phenyl-4H-3,1-benzoxazin-2-amine has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6533 (98% deuterium incorporation), at least 6600 (99% deuterium incorporation), or at least 6633.3 (99.5% deuterium incorporation).

In embodiments, the compounds of Formulae I-II described hereinabove, are enantiomerically pure deuterated S-etifoxine isomer. In the compositions provided herein, deuterated enantiomerically pure S-etifoxine analog or a pharmaceutically acceptable salt, solvate, or prodrug thereof can be present with other active or inactive ingredients. For example, a pharmaceutical composition comprising deuterated enantiomerically pure S-etifoxine analog can comprise, for example, about 90% excipient and about 10% enantiomerically pure deuterated S-etifoxine analog. In certain embodiments, the enantiomerically pure S-etifoxine deuterated analog in such compositions can, for example, comprise, at least about 99.9% by weight S-etifoxine deuterated analog and at most about 0.1% by weight R-etifoxine deuterated analog. In embodiments, the active ingredient can be formulated with little or no excipient or carrier.

In one aspect, the compounds of Formulae I-II described hereinabove, are enantiomerically pure deuterated R-etifoxine isomer. In the compositions provided herein, deuterated enantiomerically pure R-etifoxine analog or a pharmaceutically acceptable salt, solvate, or prodrug thereof can be present with other active or inactive ingredients. For example, a pharmaceutical composition comprising deuterated enantiomerically pure R-etifoxine analog can comprise, for example, about 90% excipient and about 10% enantiomerically pure deuterated R-etifoxine analog. In embodiments, the enantiomerically pure R-etifoxine deuterated analog in such compositions can, for example, comprise, at least about 99.9% by weight R-etifoxine deuterated analog and at most about 0.1% by weight R-etifoxine deuterated analog. In embodiments, the active ingredient can be formulated with little or no excipient or carrier.

In embodiments, methods of treating a developmental disorder and/or a seizure disorder are provided which include administering etifoxine to a patient in need thereof.

In embodiments, methods of treating a developmental disorder and/or a seizure disorder are provided which include administering R-etifoxine to a patient in need thereof.

In embodiments, methods of treating a developmental disorder and/or a seizure disorder are provided which include administering an enantiomerically pure R-etifoxine to a patient in need thereof.

In embodiments, methods of treating a developmental disorder and/or a seizure disorder are provided which include administering S-etifoxine to a patient in need thereof.

In embodiments, methods of treating a developmental disorder and/or a seizure disorder are provided which include administering an enantiomerically pure S-etifoxine to a patient in need thereof.

In embodiments, methods of treating a developmental disorder and/or a seizure disorder are provided which include administering a deuterated analog of etifoxine to a patient in need thereof.

In embodiments, methods of treating a developmental disorder and/or a seizure disorder are provided which include administering a deuterated analog of R-etifoxine to a patient in need thereof.

In embodiments, methods of treating a developmental disorder and/or a seizure disorder are provided which include administering a deuterated analog of an enantiomerically pure R-etifoxine to a patient in need thereof.

In embodiments, methods of treating a developmental disorder and/or a seizure disorder are provided which include administering a deuterated analog of S-etifoxine to a patient in need thereof.

In embodiments, methods of treating a developmental disorder and/or a seizure disorder are provided which include administering a deuterated analog of an enantiomerically pure S-etifoxine to a patient in need thereof.

In embodiments, methods of treating a developmental disorder and/or a seizure disorder are provided which include administering a deuterated analog of etifoxine as depicted in any of the Formulae described hereinabove to a patient in need thereof.

In embodiments, methods of treating a developmental disorder and/or a seizure disorder are provided which include administering an etifoxine, a deuterated analog of etifoxine, or a pharmaceutically acceptable salt, solvate, or prodrug thereof to a patient in need thereof in an amount of about 0.1 mg to about 2000 mg. In embodiments, the methods of treating a developmental disorder and/or seizure disorder include administering at least one etifoxine selected from R-etifoxine, S-etifoxine, and combinations thereof in an amount of about 0.1 mg to about 2000 mg. In embodiments, methods of treating a developmental disorder and/or a seizure disorder include administering at least one deuterated analog of etifoxine selected from Formulas I-VII described herein and combination thereof in an amount of about 0.1 mg to about 2000 mg. In embodiments, methods of treating a developmental disorder and/or a seizure disorder include administering at least one deuterated analog of etifoxine selected from deuterated R-etifoxine, deuterated S-etifoxine, and combinations thereof in an amount of about 0.1 mg to about 2000 mg.

In embodiments, an etifoxine, a deuterated analog of etifoxine, or a pharmaceutically acceptable salt, solvate, or prodrug thereof is administered to a patient in an amount which is effective (an "effective amount") to provide improvement in one or more symptoms of the developmental and/or seizure disorders mentioned above. In embodiments, methods of treating a developmental and/or seizure disorder described herein include administering an etifoxine, a deuterated analog of etifoxine, or a pharmaceutically acceptable salt, solvate, or prodrug thereof to a patient in need thereof in an amount which is effective to provide improvement in next day functioning of the patient.

In embodiments, the amount of an etifoxine, a deuterated analog of etifoxine, or a pharmaceutically acceptable salt, solvate, or prodrug thereof administered daily can be between about 10 mg and 1000 mg or more. For example, the daily dosage can be 10 mg, 15 mg, 20 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg or 1600 mg. In general, the daily dosage should not exceed 1600 mg. However, there are situations when amounts greater than 1600 mg can be administered. In embodiments, an adult dose can be about 300-400 mg per day and can be increased to 600 mg per day. Dosages can be lower for infants and children than for adults. In embodiments, a pediatric dose can be about 10-500 mg per day in 3 to 4 divided doses.

In embodiments, an etifoxine, a deuterated analog of etifoxine, or a pharmaceutically acceptable salt, solvate, or prodrug thereof can be administered one, two, three, four or more times daily in divided doses. In embodiments, an etifoxine, a deuterated analog of etifoxine, or a pharmaceutically acceptable salt, solvate, or prodrug thereof is administered via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories. In embodiments, rectal suppositories containing an etifoxine, a deuterated analog of etifoxine, or a pharmaceutically acceptable salt, solvate, or prodrug thereof can be administered in a dose range of about 450-600 mg per day in adults and about 10-400 mg per day in infants and children. Etifoxine, a deuterated analog of etifoxine, or a pharmaceutically acceptable salt, solvate, or prodrug thereof may be administered intravenously to adults, infants and children, e.g., to treat developmental disorders and/or seizure disorders. In embodiments, unit doses in connection with any route of administration can include 0.005 mg, 0.01 mg, 0.025 mg, 0.05 mg, 0.075 mg, 0.1 mg, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8 mg, 8.25 mg, 8.5 mg, 8.75 mg, 9 mg, 9.25 mg, 9.5 mg, 9.75 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg or 500 mg an etifoxine, a deuterated analog of etifoxine, or a pharmaceutically acceptable salt, solvate, or prodrug thereof. In embodiments, such amounts may be administered one or more times daily.

In embodiments, etifoxine, a deuterated analog of etifoxine, or a pharmaceutically acceptable salt, solvate, or prodrug thereof can be formulated in oral capsules or tablets comprising about 15 mg, about 25 mg, about 40 mg, about 50 mg, about 75 mg, about 100 mg, about 120 mg, about 150 mg, about 175 mg, about 200 mg, about 250 mg or about 300 mg of the active ingredient.

In embodiments, R-etifoxine and/or S-etifoxine can be formulated in oral capsules or tablets comprising about 15 mg, about 25 mg, about 40 mg, about 50 mg, about 75 mg, about 100 mg, about 120 mg, about 150 mg, about 175 mg, about 200 mg, about 250 mg or about 300 mg of the active ingredient.

In embodiments, deuterated etifoxine, deuterated R-etifoxine, and/or deuterated S-etifoxine can be formulated in oral capsules or tablets comprising about 15 mg, about 25 mg, about 40 mg, about 50 mg, about 75 mg, about 100 mg, about 120 mg, about 150 mg, about 175 mg, about 200 mg, about 250 mg or about 300 mg of the active ingredient.

In embodiments, methods of treating a developmental disorder and/or a seizure disorder are provided which include administering to a patient in need thereof a pharmaceutical composition including etifoxine, a deuterated analog of etifoxine, or a pharmaceutically acceptable salt, solvate, or prodrug thereof wherein the composition provides improvement in one or more symptoms of the disorder for more than 6 hours after administration to the patient. In embodiments, methods of treating a developmental disorder and/or a seizure disorder are provided which include administering to a patient in need thereof a pharmaceutical composition including etifoxine, a deuterated analog of etifoxine, or a pharmaceutically acceptable salt, solvate, or prodrug thereof wherein the composition provides improvement in one or more symptoms of the disorder for more than 8, 10, 12, 14, 16, 18, 20, 22 or 24 hours after administration to the patient. In embodiments, the pharmaceutical compositions provide improvement of next day functioning of the patient. For example, the pharmaceutical compositions may provide improvement in one or more symptoms of the disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, methods include treating a developmental disorder and/or a seizure disorder by administering to a subject in need thereof at least one compound selected from the group consisting of etifoxine, R-etifoxine, S-etifoxine, deuterated etifoxine, deuterated R-etifoxine, deuterated S-etifoxine, combinations thereof, and pharmaceutically acceptable salts, solvates, hydrates, or prodrugs thereof.

In embodiments, methods include treating a developmental disorder and/or a seizure disorder by administering to a subject in need thereof about 0.05 mg to about 1500 mg of a compound selected from the group consisting of etifoxine, a deuterated analog of etifoxine, or a pharmaceutically acceptable salt, solvate, or prodrug thereof. In embodiments, methods include treating a developmental disorder and/or a seizure disorder by administering to a subject in need thereof about 0.07 mg to about 1000 mg of a compound selected from the group consisting of etifoxine, a deuterated analog of etifoxine, or a pharmaceutically acceptable salt, solvate, or prodrug thereof. In embodiments, the amount of a compound selected from the group consisting of etifoxine, a deuterated analog of etifoxine, or a pharmaceutically acceptable salt, solvate, or prodrug thereof can be between 0.001 and 1500 mg/day, or 0.05 mg/kg/day to 500 mg/kg/day, for treatment of a developmental disorder and/or a seizure disorder. For example, the daily dosage can be, e.g., in the range of about 0.05 to 1500 mg, 0.05 to 1250 mg, 0.05 to 1000 mg, 0.05 to 750 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 1500 mg, 0.5 to 1250 mg, 0.5 to 1000 mg, 0.5 to 750 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

Suitable dosages may be administered to a subject having a developmental disorder and/or a seizure disorder once, twice, three or four times daily, every other day, once weekly, or once a month. In embodiments, at least one compound selected from the group consisting of etifoxine, a deuterated analog of etifoxine, or a pharmaceutically acceptable salt, solvate, or prodrug thereof is administered to a subject having a developmental disorder and/or a seizure disorder twice a day, (e.g., morning and evening), or three times a day (e.g., at breakfast, lunch, and dinner), at a dose of 1-50 mg/administration. In embodiments, a compound selected from the group consisting of etifoxine, a deuterated analog of etifoxine, or a pharmaceutically acceptable salt, solvate, or prodrug thereof is administered to a subject having a developmental disorder and/or a seizure disorder 600 mg/per day, 550 mg/per day, 500 mg/per day, 450 mg/per day, 400 mg/per day, 350 mg/per day, 300 mg/per day, 250 mg/per day, 240 mg/per day, 230 mg/per day, 225 mg/per day, 220 mg/per day, 210 mg/per day, 200 mg/per day, 190 mg/per day, 180 mg/per day, 170 mg/per day, 160 mg/per day, 150 mg/per day, 140 mg/per day, 130 mg/per day, 120 mg/per day, 110 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose can be about 0.05 to 500 mg per day and can be increased to 750 mg per day. Dosages can be lower for infants and children than for adults. In embodiments, an infant or pediatric dose can be about 0.1 to 50 mg per day once or in 2, 3 or 4 divided doses. In embodiments, a pediatric dose can be 0.75 mg/kg/day to 1.5 mg/kg/day. In embodiments, the subject may be started at a low dose and the dosage is escalated over time.

In embodiments, provided herein are methods of treating a seizure disorder including administering to a subject in need thereof a pharmaceutical composition including at least one compound selected from the group consisting of etifoxine, a deuterated analog of etifoxine, or a pharmaceutically acceptable salt, solvate, or prodrug thereof, after a warning sign of an impending seizure is detected to reduce or prevent seizure activity.

An effective amount or therapeutically effective amount can be a dosage sufficient to treat, inhibit, or alleviate one or more symptoms of a developmental disorder and/or seizure disorder such as reducing the frequency or severity of seizures, reducing behavior abnormalities (or otherwise improving behavior); or to provide a desired pharmacologic and/or physiologic effect, for example, reducing, inhibiting, or reversing one or more of the underlying pathophysiological mechanisms underlying the neurological dysfunction, increasing dopamine levels or signaling, or a combination thereof. The precise dosage will vary according to a variety of factors such as subject-dependent variables (e.g., age, immune system health, clinical symptoms etc.). In embodiments, a subject may be started at a low dose and the dosage is escalated. In this manner, it can be determined if the drug is well tolerated in the subject. Dosages can be lower for children than for adults.

In embodiments, the methods described herein are effective to reduce, delay, or prevent one or more other clinical symptoms of a developmental disorder such as Fragile X syndrome or a seizure disorder, such as acute repetitive seizures. For example, the effect of etifoxine, R-etifoxine, S-etifoxine, deuterated etifoxine, deuterated R-etifoxine, deuterated S-etifoxine, combinations thereof, pharmaceutically acceptable salts thereof, derivative or analogue thereof, on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

In embodiments, the pharmaceutical compositions described herein may be administered once daily, twice daily, three times daily, four times daily, or every other day. In embodiments, the pharmaceutical compositions described herein may be administered by continuous infusion. In embodiments, a pharmaceutical composition described herein is provided to the subject in the morning. In embodiments, a pharmaceutical composition described herein is provided to the subject in the evening. In embodiments, a pharmaceutical composition described herein is provided to the subject once in the evening and once in the morning. In embodiments, a pharmaceutical composition described herein is provided to the subject once in the morning, once in the afternoon and once in the evening.

Suitable methods of administration include, in addition to the infusion methods described above, oral, buccal, sublingual, rectal, topical, intranasal, vaginal, parenteral, combinations thereof, and the like.

In embodiments, as mentioned previously, pharmaceutical compositions herein may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Subjects with seizure disorders may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are within the purview of those skilled in the art. For example, coated slow release beads or granules ("beads" and "granules" are used interchangeably herein) in which at least one compound selected from the group consisting of etifoxine, a deuterated analog of etifoxine, or a pharmaceutically acceptable salt, solvate, or prodrug thereof, is applied to beads, e.g., confectioners nonpareil beads, and then coated with conventional release retarding materials such as waxes, enteric coatings and the like. In embodiments, beads can be formed in which at least one compound selected from the group consisting of etifoxine, a deuterated analog of etifoxine, or a pharmaceutically acceptable salt, solvate, or prodrug thereof is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as etifoxine, a deuterated analog of etifoxine, or a pharmaceutically acceptable salt, solvate, or prodrug thereof, at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are within the purview of those skilled in the art. For example, coated delayed release beads or granules in which etifoxine, a deuterated analog of etifoxine, or a pharmaceutically acceptable salt, solvate, or prodrug thereof, is applied to beads, e.g., confectioners nonpareil beads, and then coated with conventional release delaying materials such as waxes, enteric coatings and the like. In embodiments, beads can be formed in which etifoxine, a deuterated analog of etifoxine, or a pharmaceutically acceptable salt, solvate, or prodrug thereof, is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of etifoxine, a deuterated analog of etifoxine, or a pharmaceutically acceptable salt, solvate, or prodrug thereof, can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., EUDRAGIT® coatings such methacrylic acid and methyl methacrylate polymers and others. The granules can be contained in capsules or compressed into tablets.

In embodiments, etifoxine, a deuterated analog of etifoxine, or a pharmaceutically acceptable salt, solvate, or prodrug thereof, is incorporated into porous inert carriers that provide delayed release profiles. In embodiments, the porous inert carriers incorporate channels or passages from which the drug diffuses into surrounding fluids. In embodiments, etifoxine, a deuterated analog of etifoxine, or a pharmaceutically acceptable salt, solvate, or prodrug thereof, is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, pharmaceutical compositions described herein are suitable for parenteral administration, including, e.g., intramuscular (i.m.), intravenous (i.v.), subcutaneous (s.c.), intraperitoneal (i.p.), or intrathecal (i.t.). Parenteral compositions must be sterile for administration by injection, infusion or implantation into the body and may be packaged in either single-dose or multi-dose containers. In embodiments, liquid pharmaceutical compositions for parenteral administration to a subject include an active substance, e.g., etifoxine, a deuterated analog of etifoxine, or a pharmaceutically acceptable salt, solvate, or prodrug thereof, in any of the respective amounts described above. In embodiments, the pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a subject in need thereof.

The pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of (etifoxine, a deuterated analog of etifoxine, or a pharmaceutically acceptable salt, solvate, or prodrug thereof, used in the composition. Thus, parenteral compositions are provided wherein there is no incompatibility between any of the components of the dosage form.

In embodiments, parenteral compositions including etifoxine, a deuterated analog of etifoxine, or a pharmaceutically acceptable salt, solvate, or prodrug thereof, include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, parenteral compositions include etifoxine, a deuterated analog of etifoxine, or a pharmaceutically acceptable salt, solvate, or prodrug thereof, and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, thrice or four or more times daily, or continuously depending on the subject's needs.

In embodiments, parenteral compositions of an active substance, e.g., (etifoxine, a deuterated analog of etifoxine, or a pharmaceutically acceptable salt, solvate, or prodrug thereof, are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, the etifoxines described herein can be administered in combination with one or more additional active ingredients, such as other agents effective for CNS disorders or mental disorders. Such agents include, but are not limited to the following: serotonin receptor (e.g., 5-HT1A) agonists and antagonists; neurokinin receptor antagonists or corticotropin releasing factor receptor (CRF1) antagonists; melatonin receptor agonists; and nicotinic agonists, muscarinic agents, acetylcholinesterase inhibitors and dopamine receptor agonists. In certain embodiments, the other active agents are arylpiperazines, for example buspirone, gepirone, ipsapirone and tondospirone; benzodiazepine derivatives such as alprazolam, bromazepam, camazepam, chlordiazepoxide, clobazam, clorazepate, chotiazepam, cloxazolam, diazepam, ethyl loflazepate, etizolam, fluidazepam, flutazolam, flutoprazepam, halazepam, ketazolam, lorazepam, loxapine, medazepam, metaclazepam, mexazolam, nordazepam, oxazepam, oxazolam, pinazepam, prazepam and tofisopam; carbamates such as cyclarbamate, emylcamate, hydroxyphenamate, meprobamate, phenprobamate and tybamate; and others such as alpidem, benzoctamine, captodiamine, chlormezanone, flesinoxan, fluoresone, glutamic acid, hydroxyzine, lesopitron, mecloralurea, mephenoxalone, mirtazepine, oxanamide, phenaglycodol, suriclone and zatosetron.

In embodiments, the other additional active agent is fluoxetine (Prozac®), paroxetine (Paxil®), sertraline (Zoloft®), citalopram (Celexa®) orfluvoxamine (Luvox®), venlafaxine (Effexor®), mirtazapine (Remeron®), nefazodone (Serzone®), trazodone (Desyrel®), venlafaxine (Effexor®), bupropion (Wellbutrin®), lithium (Eskalith, Lithobid®), valproate (Depakene®, Depakote®) carbamazepine (Epitol, Tegretol®), neurontin (Gabapentin®), lamictal (Lamotrigine®), ziprasidone (Geodon®), risperidone (Risperdal®), quetiapine (Seroquel®), phenelzine (Nardil®), tranylcypromine (Parnate®), amitriptyline (Elavil®), protriptyline (Vivactil®), desipramine (Norpramin®), nortriptyline (Aventyl®, Pamelor®), trimipramine (Surmontil®), perphenazine (Triavil®), maprotiline (Ludiomil®), mirtazapine (Remeron®), methylphenidate (Ritalin®) or dextroamphetamine (Dexedrine®).

In embodiments, the other additional active agent is an antidepressant, such as a tricyclic antidepressant ("TCA"), a selective serotonin reuptake inhibitor ("SSRI"), a serotonin and noradrenaline reuptake inhibitor ("SNRI"), a dopamine reuptake inhibitor ("DRI"), a noradrenaline reuptake inhibitor ("NRI"), a dopamine and noradrenaline reuptake inhibitor ("DNRI"), a monoamine oxidase inhibitor ("MAOI"), an alpha-2-receptor blocker or another antidepressant.

Exemplary TCAs include, but are not limited to, amitriptyline (Elavil®), amoxapine (Asendin®), clomipramine (Anafranil®), desipramine (Norpramin®), doxepin (Adapin®, Sinequan®), imipramine (Tofranil®), maprotiline (Ludiomil®), nortriptyline (Aventyl®, Pamelor®), protriptyline (Vivactil®) and trimipramine (Surmontil®).

Exemplary SSRIs include, but are not limited to, sertraline (Zoloft®), sertraline metabolite demethylsertraline, fluoxetine (Prozac®), norfluoxetine (fluoxetine desmethyl metabolite), fluvoxamine (Luvox®), paroxetine (Seroxat®, Paxil®) and its alternative formulation, Paxil-CR®, citalopram (Celexa®), citalopram metabolite desmethylcitalopram, escitalopram (Lexapro®), d,l-fenfluramine (Pondimin®), femoxetine, ifoxetine, cyanodothiepin, litoxetine, cericlamine and dapoxetine.

Exemplary NRIs include, but are not limited to, reboxetine (Edronax®) and all isomers of reboxetine, i.e., (R/R,S/S,R/S,S/R), desipramine (Norpramin®), maprotiline (Ludiomil®), lofepramine (Gamanil®), oxaprotiline, fezolamine, atomoxetine (Strattera®), nomifensine (Merital®), viloxazine (Vivalan®), or mianserin (Bolvidon®).

Exemplary SNRIs include, but are not limited to, venlafaxine (Effexor®), venlafaxine metabolite O-desmethylvenlafaxine, clomipramine (Anafranil®), clomipramine metabolite desmethylclomipramine, duloxetine (Cymbalta®), milnacipran, imipramine (Tofranil® or Janimine®) and nefazaodone (Serzone®).

Exemplary MAOIs include, but are not limited to, phenelzine (Nardil®), tranylcypromine (Parnate®), isocarboxazid (Marplan®) and selegiline (Emsam®, Eldepryl®).

Exemplary alpha-2-receptor blockers include, but are not limited to, mirtazapine (Remeron®, Remeron Soltab®).

Other useful antidepressants include buproprion (Wellbutrin®, Zyban®), buproprion metabolite hydroxybuproprion and trazodone (Desyrel®).

In embodiments, the additional active agent is gaboxadol.

In embodiments, the additional active agent is an allosteric modulator. Allosteric modulators may include a neurosteroid, e.g., ganaxolone or allopregnanolone, a benzodiazepine, e.g., midazolam, clobazam, clonazepam, diazepam, lorazepam, flurazepam, lorazepam etc., or a potassium channel opener, e.g., retigabine or flupirtine.

In embodiments the additional active agent is:

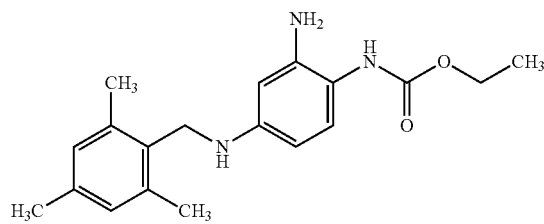 [SMILES: CCOC(=O)Nc1ccc(NCc2c(C)cc(C)cc2C)cc1N]

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of developmental disorders and/or seizure disorders such as epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (also called serial or cluster seizures), measured relative to at least one symptom of the foregoing disorders.

"Improvement in next day functioning" or "wherein there is improvement in next day functioning" refers to improvement after waking from an overnight sleep period wherein the beneficial effect of administration of the etofixines described herein applies to at least one symptom of a syndrome or disorder herein and is discernable, either subjectively by a subject or objectively by an observer, for a period of time, e.g., 2 hours, 3 hours, 4 hours, 5 hours, 6 hours, 12 hours, 24 hours, etc. after waking.

"Treating", "treatment" or "treat" can refer to the following: alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating", "treat" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating", "treat" or "treatment" also refers to inhibiting the disease or condition, e.g., arresting or reducing its development or at least one clinical or subclinical symptom thereof "Treating", "treat" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount", previously referred to, can also mean a dosage sufficient to alleviate one or more symptoms of a syndrome, disorder, disease, or condition being treated, or to otherwise provide a desired pharmacological and/or physiologic effect. "Effective amount" or "therapeutically effective amount" may be used interchangeably herein.

"Co-administered with", "administered in combination with", "a combination of" or "administered along with" may be used interchangeably and mean that two or more agents are administered in the course of therapy. The agents may be administered together at the same time or separately in spaced apart intervals. The agents may be administered in a single dosage form or in separate dosage forms.

"Subject in need thereof" may include individuals that have been diagnosed with a developmental disorder and/or seizure disorder such as Angelman syndrome, Fragile X syndrome, epilepsy, epilepsy with generalized tonic-clonic seizures, epilepsy with myoclonic absences, frontal lobe epilepsy, temporal lobe epilepsy, Landau-Kleffner Syndrome, Rasmussen's syndrome, Dravet syndrome, Doose syndrome, CDKL5 disorder, infantile spasms (West syndrome), juvenile myoclonic epilepsy (JME), vaccine-related encephalopathy, intractable childhood epilepsy (ICE), Lennox-Gastaut syndrome (LGS), Rett syndrome, Ohtahara syndrome, CDKL5 disorder, childhood absence epilepsy, essential tremor, acute repetitive seizures, benign rolandic epilepsy, status epilepticus, refractory status epilepticus, super-refractory status epilepticus (SRSE), PCDH19 pediatric epilepsy, drug withdrawal induced seizures, alcohol withdrawal induced seizures, increased seizure activity or breakthrough seizures (also called serial or cluster seizures). The methods may be provided to any individual including, e.g., wherein the subject is a neonate, infant, a pediatric subject (6 months to 12 years), an adolescent subject (age 12-18 years) or an adult (over 18 years). Subjects include mammals.

"Prodrug" refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" may be used interchangeably and refer to a compound that possesses the same core as the parent compound, but may differ from the parent compound in bond order, the absence or presence of one or more atoms and/or groups of atoms, and combinations thereof. Enantiomers are examples of derivatives. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

The term "pharmaceutically acceptable salt", as used herein, refers to derivatives of the compounds defined herein, wherein the parent compound is modified by making acid or base salts thereof. Example of pharmaceutically acceptable salts include, but are not limited to, nontoxic base addition salts with inorganic bases. Suitable inorganic bases such as alkali and alkaline earth metal bases include metallic cations such as sodium, potassium, magnesium, calcium and the like. The pharmaceutically acceptable salts can be synthesized from the parent compound by conventional chemical methods.

It should be understood that the examples and embodiments provided herein are exemplary examples embodiments. Those skilled in the art will envision various modifications of the examples and embodiments that are consistent with the scope of the disclosure herein. Such modifications are intended to be encompassed by the claims.

What is claimed is:

1. A method of treating autism comprising administering to a patient in need thereof a therapeutically effective dosage of etifoxine or a pharmaceutically acceptable salt thereof once daily, wherein the method provides improvement in one or more symptoms of autism.

2. The method of claim 1, wherein the patient is administered between 50 to 400 mg etifoxine or a pharmaceutically acceptable salt thereof.

3. The method of claim 1, wherein the patient is administered between 50 to 300 mg etifoxine or a pharmaceutically acceptable salt thereof.

4. The method of claim 1, wherein the patient is administered between 50 to 200 mg etifoxine or a pharmaceutically acceptable salt thereof.

5. The method of claim 4, wherein the method provides improvement for more than 6 hours.

6. The method of claim 3, wherein the method provides improvement for more than 8 hours.

7. The method of claim 1, wherein the patient is administered 50 mg etifoxine or a pharmaceutically acceptable salt thereof.

8. The method of claim 1, wherein the patient is administered 100 mg etifoxine or a pharmaceutically acceptable salt thereof.

9. The method of claim 1, wherein the patient is administered 150 mg etifoxine or a pharmaceutically acceptable salt thereof.

10. The method of claim 1, wherein the patient is administered 200 mg etifoxine or a pharmaceutically acceptable salt thereof.

11. The method of claim 1, wherein the patient is administered 300 mg etifoxine or a pharmaceutically acceptable salt thereof.

12. The method of claim 1, wherein the patient is administered 400 mg etifoxine or a pharmaceutically acceptable salt thereof.

13. A method of treating autism comprising administering to a patient in need thereof a therapeutically effective dosage of etifoxine or a pharmaceutically acceptable salt thereof once daily, wherein the method provides improvement in irritability associated with autism.

14. The method of claim 13, wherein the patient is administered between 50 to 400 mg etifoxine or a pharmaceutically acceptable salt thereof.

15. The method of claim 13, wherein the patient is administered between 50 to 300 mg etifoxine or a pharmaceutically acceptable salt thereof.

16. The method of claim 13, wherein the patient is administered between 50 to 200 mg etifoxine or a pharmaceutically acceptable salt thereof.

17. The method of claim 14, wherein the method provides improvement for more than 6 hours.

18. The method of claim 16, wherein the method provides improvement for more than 8 hours.

19. The method of claim 13, wherein the patient is administered 50 mg etifoxine or a pharmaceutically acceptable salt thereof.

20. The method of claim 13, wherein the patient is administered 100 mg etifoxine or a pharmaceutically acceptable salt thereof.

21. The method of claim 13, wherein the patient is administered 150 mg etifoxine or a pharmaceutically acceptable salt thereof.

22. The method of claim 13, wherein the patient is administered 200 mg etifoxine or a pharmaceutically acceptable salt thereof.

23. The method of claim 13, wherein the patient is administered 300 mg etifoxine or a pharmaceutically acceptable salt thereof.

24. The method of claim 13, wherein the patient is administered 400 mg etifoxine or a pharmaceutically acceptable salt thereof.

25. The method of claim 1, wherein the patient is administered between 10 to 100 mg etifoxine or a pharmaceutically acceptable salt thereof.

26. The method of claim 1, wherein the patient is administered between 25 to 100 mg etifoxine or a pharmaceutically acceptable salt thereof.

27. The method of claim 1, wherein the patient is administered 10 mg etifoxine or a pharmaceutically acceptable salt thereof.

28. The method of claim 1, wherein the patient is administered 25 mg etifoxine or a pharmaceutically acceptable salt thereof.

29. The method of claim 13, wherein the patient is administered between 10 to 100 mg etifoxine or a pharmaceutically acceptable salt thereof.

30. The method of claim 13, wherein the patient is administered between 25 to 100 mg etifoxine or a pharmaceutically acceptable salt thereof.

31. The method of claim 13, wherein the patient is administered 10 mg etifoxine or a pharmaceutically acceptable salt thereof.

32. The method of claim 13, wherein the patient is administered 25 mg etifoxine or a pharmaceutically acceptable salt thereof.

* * * * *